United States Patent
Shyadligeri et al.

(10) Patent No.: US 6,646,097 B1
(45) Date of Patent: Nov. 11, 2003

(54) METHOD FOR PURIFYING 1,1-BIS(4'-HYDROXY-3'-METHYLPHENYL) CYCLOHEXANE AND METHODS OF PRODUCING POLYCARBONATES THEREFROM

(75) Inventors: Ashok Shyadligeri, Bangalore (IN); Gary C. Davis, Albany, NY (US); Debjani Kapila, Bangalore (IN); Ramesh Krishnamurti, Bangalore (IN); A. S. Radhakrishna, Bangalore (IN); Veeraraghavan Srinivasan, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/065,573

(22) Filed: Oct. 31, 2002

(51) Int. Cl.$^7$ ............................................. C08G 64/00
(52) U.S. Cl. .................. 528/196; 528/198; 568/727; 568/728; 568/806
(58) Field of Search ................ 528/196, 198; 568/727, 728, 806

(56) References Cited

U.S. PATENT DOCUMENTS

| | | |
|---|---|---|
| 4,113,974 A | 9/1978 | Mark et al. |
| 4,217,438 A | 8/1980 | Brunelle et al. |
| 4,242,527 A | 12/1980 | Mark et al. |
| 4,304,899 A | 12/1981 | Mark et al. |
| 4,320,234 A | 3/1982 | Mark et al. |
| 6,001,953 A | 12/1999 | Davis et al. |
| 6,258,922 B1 * | 7/2001 | Okamoto et al. ............ 528/196 |
| 6,395,364 B1 * | 5/2002 | Davis et al. ................ 428/64.1 |
| 6,395,864 B1 * | 5/2002 | Kuhling et al. ............. 528/196 |

OTHER PUBLICATIONS

JP1226841. Publication date: Sep. 11, 1989. English Abstract. 1 page.
JP2048543. Publication date: Feb. 19, 1990. English Abstract. 1 page.

* cited by examiner

Primary Examiner—Terressa M. Boykin

(57) ABSTRACT

A method for purifying 1,1-bis(4'-hydroxy-3'-methylphenyl) cyclohexane comprises dissolving said 1,1-bis(4'-hydroxy-3'-methylphenyl)cyclohexane in a first solvent consisting essentially of an alcohol to form a first solution; filtering said first solution; adding a second solvent consisting essentially of water to the filtered first solution to form a second solution, wherein said second solution comprises about 40 parts to about 95 parts of the first solvent per 100 parts of the combined weight of the first and second solvents; crystallizing said 1,1-bis(4'-hydroxy-3'-methylphenyl) cyclohexane from said second solution to form a first crystalline product; dissolving said first crystalline product in a third solvent to form a third solution, wherein the third solvent comprises an aromatic compound; and crystallizing said 1,1-bis(4'-hydroxy-3'-methylphenyl)cyclohexane from said third solution to produce a second crystalline product.

22 Claims, No Drawings

METHOD FOR PURIFYING 1,1-BIS(4'-HYDROXY-3'-METHYLPHENYL) CYCLOHEXANE AND METHODS OF PRODUCING POLYCARBONATES THEREFROM

BACKGROUND

This disclosure generally relates to a method for purifying a 1,1-bis(4'-hydroxy-3'-methylphenyl) cyclohexane monomer, and polycarbonates produced utilizing the purified monomer.

The compound, 1,1-bis(4'-hydroxy-3'-methylphenyl) cyclohexane (hereinafter referred to as DMBPC), can be used as a monomer for preparing polycarbonates used in making optical data storage products. DMBPC is generally prepared by reacting cyclohexanone with o-cresol in the presence of a condensation catalyst. During this reaction, side products are created which, if not removed, can result in DMBPC having an unacceptable purity for use as a monomer or as a comonomer for producing polycarbonates. The undesirable side products or impurities include both inorganic and organic species. For example, the impurities can hinder polymerization resulting in low molecular weight polycarbonates that exhibit undesirable physical properties, such as increased brittleness. Furthermore, the impurities in the DMBPC monomer can undesirably produce discoloration in the polycarbonates, thereby affecting the transparency of the product.

BRIEF SUMMARY

Disclosed herein is a method for purifying 1,1-bis(4'-hydroxy-3'-methylphenyl) cyclohexane. The method comprises dissolving said 1,1-bis(4'-hydroxy-3'-methylphenyl) cyclohexane in a first solvent consisting essentially of an alcohol to form a first solution; filtering said first solution; adding a second solvent consisting essentially of water to the filtered first solution to form a second solution, wherein said second solution comprises about 40 parts to about 95 parts of the first solvent per 100 parts of the combined weight of the first and second solvents; crystallizing said 1,1-bis(4'-hydroxy-3'-methylphenyl)cyclohexane from said second solution to form a first crystalline product; dissolving said first crystalline product in a third solvent to form a third solution, wherein the third solvent comprises an aromatic compound; and crystallizing said 1,1-bis(4'-hydroxy-3'-methylphenyl)cyclohexane from said third solution to produce a second crystalline product.

In another embodiment, a method of producing a polycarbonate comprises-melt reacting a reaction mixture to produce a polycarbonate product, the reaction mixture comprising: a catalyst, a carbonic acid diester of the formula $(ZO)_2C=O$, wherein each Z is independently an unsubstituted or substituted alkyl radical, or an unsubstituted or substituted aryl radical; a second crystalline product of 1,1-bis(4'-hydroxy-3'-methylphenyl)cyclohexane formed by dissolving said 1,1-bis(4'-hydroxy-3'-methylphenyl) cyclohexane in a first solvent consisting essentially of an alcohol to form a first solution; filtering said first solution, and adding to the filtered first solution a second solvent consisting essentially of water to form a second solution until said second solution contains from about 40 parts to about 95 parts of said alcohol per 100 parts of the combined weight of said alcohol and water; crystallizing said 1,1-bis(4'-hydroxy-3'-methylphenyl)cyclohexane from said second solution to produce a first crystalline product; dissolving said first crystalline product in a third solvent comprising a compound having the formula $R^1R^2(C_6H_3)R^3$ to form a third solution; and crystallizing said 1,1-bis(4'-hydroxy-3'-methylphenyl)cyclohexane from said third solution to produce a second crystalline product; and at least one aromatic dihydroxy compound comonomer having the formula:

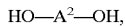
HO—$A^2$—OH, wherein $A^2$ is selected from the group consisting of divalent substituted and unsubstituted aromatic radicals.

In another embodiment, a method of producing a polycarbonate comprises interfacially reacting a reaction mixture at a temperature from about 5° C. to about 50° C., and an initial pH from about 9.5 to about 11.0 to produce a polycarbonate product, the reaction mixture comprising: phosgene, a substituted or an unsubstituted monohydric phenol having the formula $R^5$ ($C_6H_4$)OH, wherein $R^5$ comprises hydrogen and $C_1$–$C_{12}$ linear and branched alkyland cycloalkyl groups; a tertiary amine having the formula $R^6R^7R^8N$, wherein $R^6$, $R^7$, and $R^8$ selected from $C_1$–$C_{12}$ linear and branched alkyl radicals; at least one halogen-containing hydrocarbon solvent; water, an alkali metal hydroxide selected from the group consisting of lithium hydroxide, sodium hydroxide, potassium hydroxide, rubidium hydroxide, and cesium hydroxide; a second crystalline product of 1,1-bis(4'-hydroxy-3'-methylphenyl) cyclohexane formed by dissolving said 1,1-bis(4'-hydroxy-3'-methylphenyl)cyclohexane in a first solvent consisting essentially of an alcohol to form a first solution; filtering said first solution, and adding to the filtered first solution a second solvent consisting essentially of water to form a second solution until said second solution contains from about 40 parts to about 95 parts of said alcohol per 100 parts of the combined weight of said alcohol and water; crystallizing said 1,1-bis(4'-hydroxy-3'-methylphenyl)cyclohexane from said second solution to produce a first crystalline product; dissolving said first crystalline product in a third solvent comprising a compound having the formula $R^1R^2$ ($C_6H_3$)$R^3$ to form a third solution; and crystallizing said 1,1-bis(4'-hydroxy-3'-methylphenyl)cyclohexane from said third solution to produce a second crystalline product.; and at least one aromatic dihydroxy compound comonomer having the formula:

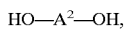
HO—$A^2$—OH, wherein $A^2$ is selected from the group consisting of divalent substituted and unsubstituted aromatic radicals; wherein the phosgene is used in an amount from about stoichiometric to about 50 mole percent excess relative to the total moles of the second crystalline product and the at least one aromatic dihydroxy compound comonomer.

The above described and other features are exemplified by the following detailed description.

DETAILED DESCRIPTION

A process for purifying 1,1-bis(4'-hydroxy-3'-methylphenyl)cyclohexane (hereinafter referred to as "DMBPC") generally includes purifying a crude DMBPC compound produced from a condensation reaction between cyclohexanone and o-cresol. As used herein, the term "crude DMBPC" is defined as the DMBPC monomer obtained directly from the condensation reaction.

The crude DMBPC is first dissolved in a solvent consisting essentially of an alcohol to form a first solution. Alcohols that are miscible with water are appropriate first solvents for dissolving the crude DMBPC. Preferred alcohols are represented by the formula $R^4OH$, wherein $R^4$ comprises a linear or branched $C_1$–$C_4$ alkyl radical. Examples of suitable alcohols that can be used include, but are not limited to, methanol, ethanol, isopropanol, n-propanol, isobutanol, n-butanol, and tert-butanol. In a specific embodiment, the alcohol is methanol. For a given first solvent, the amount of DMBPC that can be dissolved is dependent on the temperature at which the dissolution is conducted. Generally, the higher the temperature, the greater the solubility and concentration of DMBPC in the first solvent. The temperature at which the first solution is prepared can vary from about an ambient temperature to about a reflux temperature of the first solvent.

The first solution thus obtained is then filtered to remove any insoluble material. Filtration can be performed by any of the techniques generally known to those skilled in the art. A second solvent consisting essentially of water is then added to the filtered first solution to form a second solution. The amount of water to be added can vary such that the proportion of alcohol and water in the second solution are at a ratio of about 40:60 to a ratio of about 5:95 by volume, respectively. In one embodiment, the concentration of DMBPC in the second solution should be such that the crystals formed from a suibsequent cooling process do not entrain significant levels of the impurities that are to be removed from the crude DMBPC. In various other embodiments, the second solution preferably comprises about 5 parts to about 50 parts of DMBPC per 100 parts by volume of the second solvent.

The second solution is then cooled to a temperature effective to cause the DMBPC to crystallize, i.e., to form a first crystalline product. The rate of cooling can be varied over a wide range as would be apparent to those skilled in the art. In one embodiment, cooling the second solution to form the first crystalline product comprises reducing: the temperature to about an ambient temperature to about 5 degrees centrigrade (° C.).

The purity of the first crystalline product can be determined using high performance liquid chromatography (hereinafter referred to as "HPLC"), gas chromatography, and the like. HPLC is a particularly effective technique for measuring the purity of DMBPC.

The first crystalline product is then dissolved in a third solvent comprising a compound having the formula $R^1R^2(C_6H_3)R^3$, wherein $R^1$, $R^2$, and $R^3$ groups are each independently selected from the group consisting of chlorine, hydrogen, methyl, ethyl, n-propyl, isopropyl, n-butyl, isobutyl, and tert-butyl radicals. Optionally, the third solvent comprises an alkoxyaromatic compounds, such as anisole and alkyl-substituted anisoles, various mixtures comprising $C_5$ to $C_{12}$ linear and branched aliphatic hydrocarbons, and any combination of the solvents represented by the general formula, $R^1R^2(C_6H_3)R^3$, wherein $R^1$, $R^2$, and $R^3$ are as previously described. Suitable third solvents include aromatic compounds, such as benzene, toluerie, mesitylene, individual and isomeric mixture of ortho-, meta-, and para-xylenes; halogenated aromatic compounds, such as chlorobenzene, ortho-, meta-, and para-dichlorobenzene, isomeric dichlorotoluenes, bromobenzene, individual and isomeric mixtures of ortho-, meta-, and para-chlorotoluenes, and chloroxylenes; benzotrifluoride, mixtures comprising at least on of the foregoing aromatic compounds, and the like. In a specific embodiment, the third solvent comprises toluene. The factors that govern the solubility of the first crystalline product in the third solvent are believed to depend upon the amount of the first crystalline product present as well as the temperature of the third solution. Preferably, the temperature of the third solution is at about an ambient temperature to about a reflux temperature of the third solvent.

The third solution is then cooled to a temperature effective to cause the DMBPC to crystallize, i.e., to form a second crystalline product (hereinafter referred to as the "purified DMBPC"). The rate of cooling can be varied over a wide range as would be apparent to those skilled in the art. In one embodiment, cooling the third solution to form the purified DMBPC comprises reducing the temperature to about an ambient temperature to about 5° C. Preferably, the DMBPC concentration in the third solution is such that the crystals formed during the cooling process do not entrain impurities. More preferably, the third solution comprises a DMBPC concentration of about 5 parts by weight to about 50 parts by weight of DMBPC per 100 parts by volume of the third solvent. The purity of the purified DMBPC can be readily determined as previously described.

Preferably, the purified DMBPC thus obtained comprises less than about 250 parts of any combination of 1-(4'-hydroxy-3'-methylphenyl)-1-(4'-hydroxy-3',5'-dimethylphenyl)cyclohexane compound and 1,1-bis(4'-hydroxy-3',5'-dimethylphenyl) cyclohexane compound (hereinafter collectively abbreviated as "TMBPC") as an impurity, per million parts of the second-crystalline product, with less than about 100 parts even more preferred. Furthermore, the purified DMBPC preferably comprises less than about 3000 parts of a 1-(4'-hydroxy-3'-methylphenyl)-1-(2'-hydroxy-3'-methylphenyl)cyclohexane compound as an impurity per million parts of the second-crystalline product, with less than about 100 parts even more preferred. The presence of these impurities in purified DMBPC should be minimized in order to prepare high molecular weight polycarbonate homopolymers and copolymers.

Polycarbonates comprising structural units derived from the second crystalline DMBPC can be prepared by methods including melt polymerization, interfacial polymerization, solid state polymerization, thin-film melt polymerization, and the like. Interfacial polymerization can also be carried out by using a bischloroformate derivative of the purified DMBPC.

Aromatic dihydroxy compounds suitable for preparing polycarbonates by reaction with the purified DMBPC comprise those of the general formula (I):

wherein $A^2$ is a divalent aromatic radical.

In one embodiment, $A^2$ preferably has a structure as shown in formula (II):

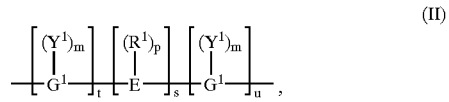

wherein $G^1$ represents an aromatic group, such as phenylene, biphenylene, naphthylene, and the like aromatic groups. E may be an alkylene or alkylidene group such as methylene, ethylene, ethylidene, propylene, propylidene, isopropylidene, butylene, butylidene, isobutylidene, amylene, amylidene, isoamylidene, and the like. Alternatively, E may consist of two or more alkylene or alkylidene groups connected by a moiety different from alkylene or alkylidene, such as an aromatic linkage, a tertiary amino linkage, an ether linkage, a carbonyl linkage, a silicon-containing linkage, a sulfur-containing linkage such as sulfide, sulfoxide, sulfone, a phosphorus-containing linkage such as phosphinyl, phosphonyl, and like linkages. In addition, E may comprise a cycloaliphatic group. $R^1$ represents hydrogen or a monovalent hydrocarbon group such as alkyl, aryl, aralkyl, alkaryl, cycloalkyl, and the like. $Y^1$ comprises a halogen (e.g., fluorine, bromine, chlorine, iodine, and the like); a nitro group; an alkenyl group, allyl group, the same as $R^1$ previously described, an oxy group such as OR, and the like. In a preferred embodiment, $Y^1$ is inert to and unaffected by the reactants and reaction conditions used to prepare the polymer. The letter "m" represents any integer from and including zero through the number of positions on $G^1$ available for substitution; "p" represents an integer from and including zero through the number of positions on E available for substitution; "t" represents an integer equal to at leastone; "s" is either zero or one; and "u" represents any integer including zero.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, adamantylidene, etc.); a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy comonomer compound shown in Formula (I) in which $A^2$ is represented by formula (II) above, when more than one $Y^1$ substituent is present, they may be the same or different. The same holds true for the $R^1$ substituent. Where "s" is zero in formula (II) and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ radicals are unsubstituted phenylene radicals; and E is an alkylidene group such as isopropylidene. In particular embodiments, both $G^1$ radicals are p-phenylene, although both may be ortho- or meta-phenylene or one ortho- or meta-phenylene and the other para-phenylene.

Some illustrative, non-limiting examples of aromatic dihydroxy compounds of formula (I) include the dihydroxy-substituted aromatic hydrocarbons disclosed by name or formula (generic or specific) in U.S. Pat. No. 4,217,438. Some particular examples of aromatic dihydroxy compound comonomers include 4,4'-(3,3,5-trimethylcyclohexylidene) diphenol; 4,4'-bis(3,5-dimethyl)diphenol; 4,4-bis(4-hydroxyphenyl)heptane; 2,4'-dihydroxydiphenylmethane; bis(2-hydroxyphenyl) methane; bis(4-hydroxyphenyl) methane; bis(4-hydroxy-5-nitrophenyl)methane; bis(4-hydroxy-2,6-dimethyl-3-methoxyphenyl)methane; 1,1-bis(4-hydroxyphenyl) ethane; 1,1-bis(4-hydroxy-2-chlorophenyl)ethane; 2,2-bis(4-hydroxyphenyl)propane (commonly known as bisphenol A); 2,2-bis(3-phenyl-4-hydroxyphenyl)propane; 2,2-bis(4-hydroxy-3-methylphenyl)propane; 2,2-bis(4-hydroxy-3-ethylphenyl) propane; 2,2-bis(4-hydroxy-3-isopropylphenyl)propane; 2,2-bis(4-hydroxy-3,5-dimethylphenyl)propane; 2,2-bis(3,5,3',5'-tetrachloro-4,4'-dihydroxyphenyl)propane; bis(4-hydroxyphenyl)cyclohexylmethane; 2,2-bis(4-hydroxyphenyl)-1-phenylpropane; 2,4'-dihydroxyphenyl sulfone; 2,6-dihydroxy naphthalene; hydroquinone; resorcinol; and $C_{1-3}$ alkyl-substituted resorcinols.

Suitable aromatic dihydroxy comonomer compounds also include those containing indane structural units such as 3-(4-hydroxyphenyl)-1,1,3-trimethylindan-5-ol, and 1-(4-hydroxyphenyl)-1,3,3-trimethylindan-5-ol.

Also included among suitable aromatic dihydroxy compound comonomers are the 2,2,2',2'-tetrahydro-1,1'-spirodiols having formula (III) as follows:

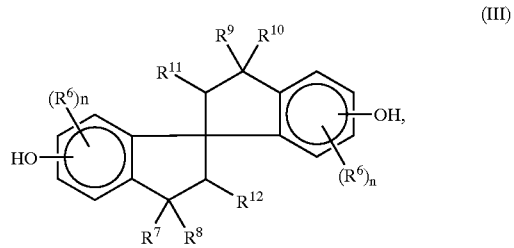

(III)

wherein each $R^6$ is independently selected from monovalent hydrocarbon radicals and halogen radicals; wherein each $R^7$, $R^8$, $R^9$, and $R_{10}$ is independently $C_{1-6}$ alkyl; wherein each $R^{11}$ and $R^{12}$ is independently hydrogen or a $C_{1-6}$ alkyl group; and wherein each n is independently selected from positive integers having avalue of from 0 to 3 inclusive. In a preferred embodiment, the 2,2,2',2'-tetrahydro-1,1'-spirodiol comprises 2,2,2',2'-tetrahydro-3,3,3',3'-tetramethyl-1,1'-spirobi[1H-indene]-6,6'-diol (sometimes known as "SBI").

The term "alkyl" as used in the various embodiments of the present disclosure is intended to designate straight chain alkyls, branched alkyls, aralkyls, cycloalkyls, and bicycloalkyl radicals. The straight chain and branched alkyl radicals, unless otherwise specified, are those containing about 1 to about 40 carbon atoms, and include as illustrative non-limiting examples methyl, ethyl, n-propyl, isopropyl, n-butyl, sec-butyl, tertiary-butyl, pentyl, neopentyl, hexyl, heptyl, octyl, nonyl, decyl, undecyl and dodecyl. In various embodiments, cycloalkyl radicals represented are those containing about 3 to about 12 ring carbon atoms. Some illustrative non-limiting examples of these cycloalkyl radicals include cyclobutyl, cyclopentyl, cyclohexyl, methylcyclohexyl, and cycloheptyl. In various embodiments, aralkyl radicals are those containing about 7, to 14 carbon atoms; these include, but are not limited to, benzyl, phenylbutyl, phenylpropyl, and phenylethyl. In various other embodiments, aromatic radicals used in the present disclosure are intended to designate monocyclic or polycyclic moieties containing about 6 to about 12 ring carbon atoms. These aryl groups may also contain one or more halogen atoms or alkyl groups substituted on the ring carbons. In most embodiments, any substituent present is not in a ring position that would prevent an appropriate aromatic radical, such as in a phenolic aromatic radical, from reacting with an appropriate olefinic group, such as in a monoterpene. Some illustrative non-limiting examples of these aromatic radicals include phenyl, halophenyl, biphlenyl, and naphthyl. In another embodiment, aromatic radicals used in the present disclosure are intended to designate aralkyl radicals containing about 7 to 14 carbon atoms.

Various embodiments of the disclosure also comprise at least one carbonic acid diester of formula (IV):

$$(ZO)_2C=O, \qquad (IV)$$

wherein each Z is independently an unsubstituted or substituted alkyl radical, or an unsubstituted or substituted aryl radical. Substituents on Z, when present, may include, but are not limited to, one or more of alkyl, halogen, chloro, bromo, fluoro, nitro, alkoxy, alkoxycarbonyl, methoxycarbonyl, ethoxycarbonyl, and cyano. Suitable carbonic acid diesters include diaryl carbonates, dialkyl carbonates and mixed aryl-alkyl carbonates such as diphenyl carbonate, bis(2,4-dichlorophenyl) carbonate, bis (2,4,5-trichlor phenyl) carbonate, bis(2-cyanophenyl) carbonate, bis(o-nitrophenyl) carbonate, (o-carbomethoxyphenyl) carbonate; (o-carboethoxyphe nyl)carbonate, ditolyl carbonate, m-cresyl carbonate, dinaphthyl carbonate, bis (diphenyl) carbonate, diethyl carbonate, dimethyl carbonate, dibutyl carbonate and dicyclohexyl carbonate, and combinations of two or more thereof. If two or more of these compounds are, utilized, preferably one of the diphenyl carbonates is a diphenyl carbonate compound.

In the preparation of the polycarbonates, the aromatic dihydroxy compound comonomers described above may be used alone, or as mixtures of two or more different aromatic dihydroxy compound comonomers. In one particular embodiment, suitable aromatic dihydroxy compound comonomers for the preparation of a polycarbonate are 2,2-bis(4-hydroxyphenyl)propane (commonly known as bisphenol A or "BPA"), and 2,2-bis(4-hydroxy-3-methylphenyl) propane, 4,4'-(1-decylidene)-bisphenol, and 2,2-bis(3-sec-butyl-4-hydroxyphenyl)propane, or combinations comprising at least one of the foregoing aromatic dihydroxy compounds.

During the manufacture of the polycarbonates by the melt transesterification method, the amount of the carbonic acid diesters preferably comprise about 0.95 moles to about 1.30 moles, and more preferably about 1.05 to about 1.15 moles, based on one mole of any combination of the purified DMBPC and the aromatic dihydroxy comonomer.

Suitable melt transesterification catalysts include alkali metal compounds, alkaline earth metal compounds, tetraorganoammonium compounds, and tetraorganophosphonium compounds, combinations comprising at least one of the foregoing catalysts.

Specific examples of alkali metal compounds or alkaline earth metal compounds include organic acid salts, inorganic acid salts, oxides, hydroxides, hydrides, and alcoholates of alkali metals and alkaline earth metals. Preferably, the catalyst is an alkali metal compound of the formula $M_1X_1$, wherein $M_1$ is selected from the group consisting of lithium, sodium, and potassium; and $X_1$ is selected from the group consisting of hydroxide and OAr, wherein Ar is a monovalent aromatic radical.

More specifically, examples of alkali metal compounds include, but are not limited to, sodium hydroxide, potassium hydroxide, lithium hydroxide, sodium bicarbonate, potassium bicarbonate, lithium bicarbonate, sodium carbonate, potassium carbonate, lithium carbonate, sodium acetate, potassium acetate, lithium acetate, lithium sttearate, sodium stearate, potassium stearate, lithium hydroxyborate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like.

Specific examples of alkaline earth metal compounds include, but are not limited to, calcium hydroxide, barium hydroxide, magnesium hydroxide, strontium hydroxide, calcium bicarbonate, barium bicarbonate, magnesium bicarbonate, strontium bicarbonate, calcium carbonate, barium carbonate, magnesium carbonate, strontium carbonate, calcium acetate, barium acetate, magnesium acetate, strontium acetate, strontium stearate, and the like.

In other e mbodiments, the catalyst is preferably a tetraorganoammonium compound of the formula $R^9NY^2$, wherein $R^9$ is a $C_1$–$C_4$ alkyl group, and $Y^2$ is hydroxide, acetate, or OAr, wherein Ar is a monovalent aromatic radical. In still other embodiments, the catalyst is a tetraorganophosphonium compound of the formula $R^9PY^2$, wherein $R^9$ is a $C_1$–$C_4$ alkyl group, and $Y^2$ is hydroxide, acetate, or OAr, wherein Ar is a monovalent aromatic radical.

Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide and the like.

Any of the catalysts disclosed above may be used as combinations of two or more substances. The catalyst may be added in a variety of forms. The catalyst may be added as a solid, for example as a powder, or it may be dissolved in a solvent, for example, in water or alcohol. The total catalyst composition is preferably about $1\times10^{-7}$ to about $2\times10^{-3}$ moles, with about $1\times10^{-6}$ to about $4\times10^{-4}$ moles more preferred for each mole of the combination of the purified DMBPC and the aromatic dihydroxy compound comonomer.

Melt polymerization can beaccomplished in a process involving one or more stages. The one stage process comprises manufacturing polycarbonates by melt polycondensation of the purified DMBPC, the aromatic dihydroxy compound comonomer, and the carbonic acid diesters in the presence of the catalysts described above. The reactor employed can be made either of glass or a metal. Optionally, the reactor walls are passivated by treatment with a suitable acidic material. If it is desirable to carry out the polymerization in a glass reactor, soaking the glass reactor in an aqueous acid medium can be used to passivate the walls of the reactor. In various embodiments, the acids for this passivation process include water solutions of mineral acids, such as hydrochloric acid, sulfuric acid, nitric acid, and the like, and organic acids, such as acetic acid, methanesulfonic acid, toluenesulfonic acid, and the like.

The reactants for the polymerization reaction can be charged into the reactor either in a solid form or in a molten form. Initial charging of reactants into the reactor and subsequent mixing of these materials under reactive conditions for polymerization is preferably conducted in an inert gas atmosphere, e.g., a nitrogen atmosphere. Mixing of the reaction mixture is accomplished by methods known in the art, such as by stirring. Reactive conditions in the present context refer to conditions comprising time, temperature, pressure and other factors that result in polymerization of the reactants.

The polymerization is conducted by subjecting the above reaction mixture to a series of temperature-pressure-time protocols. For example, the reaction temperature may be gradually raised in stages while simultaneously gradually lowering the pressure in stages. Preferably, the pressure is about atmospheric pressure at the start of the reaction to, between about atmospheric pressure and about 0.01 millibar pressure, with between about atmospheric pressure and about 0.05 millibar pressure more preferred, and with between about 300 millibars pressure and about 0.0 millibar pressure even more preferred. The temperature is preferably varied to betwen about the melting temperature of the reaction mixture and about 350° C., withetween about 180° C. and about 230° C. more preferred, with between about 230° C. and about 270° C. even more preferred, and with between about 270° C. and about 350° C. most preferred. This procedure will generally ensure that the reactants react properly to produce polycarbonates with a desired molecular weight, a desired glass transition temperature, and other desired physical properties. The reaction proceeds to build the polymer chain with production of phenol by-product. Efficient removal of the phenol by-product by application of vacuum can be used to produce polycarbonates of high molecular weight. If phenol is not removed efficiently, the phenol may undesirably cleave the growing polymer chain in the presence of the polymerization catalyst, thus leading to polymer of lower rmolecular weight. The reaction may be monitored by measuring the melt viscosity or the weight average molecular weight of the reaction mixture. After the desired melt viscosity and/or molecular weight is reached, the final polycarbonate product may be isolated from the reactor in a solid or molten form.

The method of producing polycarbonates can be operated either in a batch, semi-batch, or a continuous mode. Any reaction apparatus known in.the art may be used in conducting this reaction.

Polycar bonates prepared by melt polymerization from the purified DMBPC monomer preferably have a weight average molecular weight of at least about 30,000 Daltons, as measured by gel permeation chromatography using polystyrene as standard, with at least about 35,000 Daltons being preferred, and with at least about 40,000 Daltons/being more preferred.

The interfacial polymerization is carried out in at least one halogen-containing solvent by reacting phosgene, the purified DMBPC, and at least one aromatic dihydroxy compound comonomer having the formula:

HO—A$^2$—OH, wherein A$^2$ is selected from the group consisting of divalent substituted and unsubstituted aromatic radicals; in the presence of a suitable monohydric phenol as a chain-stopper The monohydric phenol chain-stopper preferably has a formula R$^5$(C$_6$H$_4$)OH, wherein R$^5$ comprises hydrogen and C$_1$–C$_{12}$ linear and branched alkyl and cycloalkyl a preferred embodiment, the chain-stopper is 4-cumylphenol.

The solvent used for conducting the interfacial polymerization comprises at least one halogen-containing solvent. Examples of suitable solvents that can be used include, but are not intended to be limited to, dichloromethane, 1,1-dichloroethane, 1,2-dichloroethane, chlorobenzene, and the like.

The alkali metal hydroxide is necessary for adjusting the pH at an initial reaction stage as well as throughout the course of the polymerization reaction. Generally, the alkali metal/hydroxide is introduced into the polymerization charge and the reaction mixture as an aqueous solution. Alternatively, water and the solid form of alkali metal hydroxide can also be used. Preferably, the alkali metal hydroxide is sodium hydroxide, potassium hydroxide, and combinations comprising at least one of the foregoing alkali metal hydroxides.

The quantity of phosgene that needs to be introduced into the polymerization reactor to/achieve complete conversion of the purified DMBPC and the aromatic dihydroxy compound comonomer can vary from about a stoichiometric amount to about a 50 mole percent excess relative to the total number of moles of the purified DMBPC and the aromatic dihydroxy compound comonomer, with about a 30 mole percent in excess more preferred.

Polycarbonates prepared by the interfacial polymerization method and the purified DMBPC have a weight average molecular weight of at least about 30,000 Daltons, as measured by gel permeation chromatography using polystyrene standard, and a chloroformate content from about 0.5 parts per million (ppm) to about 1.5 ppm; with at least about 315,000 Daltons and a chloroformate content from about 0.5 parts per million (ppm) to about 1.5 ppm being preferred, and with at least about 40,000 Daltons and a clhloroformate content from about 0.5 parts per million (ppm) to about 1.5 ppm being even more preferred. In other embodiments, polycarbonates prepared by the interfacial polymerization method and the purified DMBPC have a weight average molecular weight of at least about 35,000 and a chloroformate content from about 0.5 parts per million (ppm) to about 1.5 ppm, with a weight average molecular weight of at least about 35,000 and a chloroformate content from about 0.5 ppm to about 1.0 ppm more preferred.

The interfacial method of preparing polycarbonates using the purified DMBPC can also be accomplished by first converting the DMBPC to a bischloroformate, followed by reaction of the bischloroformate with an aromatic dihydroxy compound comonomer composition.

Polycarbonate compositions prepared by the melt and the interfacial polymerization methods comprise carbonate structural units of formula (V) derived from the purified DMBPC, in addition to carbonate structural units derived from the dihydroxy aromatic compound comonomer.

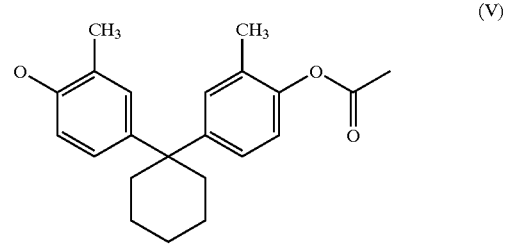

(V)

In other embodiments, the polycarbonates comprise at least one carbonate structural unit selected from the group shown in formula (VI):

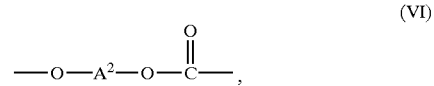

(VI)

wherein A$^2$ is a divalent aromatic radical.

The polycar onates compositions are useful for making various articles such as, for example, optical articles and films for display devices. The optical articles can function as the protective, transparent layer that covers the various recording media, such as high-density data storage media. The interfacially prepared polycarbonates have a relatively low chloroformate content (less than about 1.5 ppm). This is advantageous commercially since a reduced chloroformate content is expected to result in reduced corrosion in processing equipment employed for fabricating the articles, such as mixers, kneaders, roll mills, extruders, and the like.

The disclosure is further illustrated by the following non-limiting examples.

Weight average molecular weight (M$_w$) and number average molecular weight (M$_n$) were measured by gel permeation chromatography. Values quoted are relative to those measured for a polystyrene standard. The catalyst composition was prepared by taking appropriate aliquots of a stock solution of aqueous sodium hydroxide and 25-weight percent aqueous tetramethylammonium hydroxide. Purity was measured using HPLC, which had an experimental error in measuring the purity of ±0.66% with a 99% confidence.

EXAMPLE 1

This example describes the preparation of crude DMBPC by a HCl gas-catalyzed condensation of o-cresol with cyclohexanone.

A 2-liter three-necked round-bottomed flask, fitted with an overhead mechanical stirrer, a gas inlet, a dropping funnel, a thermometer, and a reflux condenser vented to a scrubber containing aqueous sodium hydroxide scrubber solution was assembled. The apparatus was flushed with nitrogen and pre warmed to about 45° C. using a heat gun. The reactor was then charged with ortho-cresol (1091.4 grams). The mechanical stirrer was turned on, and dry hydrogen chloride gas (generated instantaneously by reaction of 185 grams of sodium chloride with 110 grams of concentrated sulfuric acid) was then bubbled into the reaction mixture through a gas dispersion with stirring until the atmosphere in the reactor appears cloudy. This mixture was treated drop-wise with cyclohexanone (196.3 grams) with continued stirring over aperiod of about two hours. The reaction proceeded with an exotherm. The solution temperature was maintained at around 60° C. during the addition of cyclohexanone, and thereafter by using a heated oil bath. The progress of the reaction was monitored by following the disappearance of cyclohexanone using gas chromatography. After being stirred for about 24 hours, the reaction mixture was sparged with nitrogen for about 1.5 hours to remove hydrogen chloride vapors. When the headspace above the reaction mixture became clear, the reaction mixture was cooled to room temperature and filtered using a Buchner funnel. The wet filter cake was suction dried, transferred to a one-liter round-bottomed flask, and slurried with 500 ml of dichloromethane for about 40 minutes using a mechanical stirrer. The resulting suspension was filtered, and the filter cake was washed with dichloromethane (250 milliliters (ml)), suction-dried, and then dried overnight in a vacuum oven maintained at 90° C. and about 30 millibar of mercury. Crude DMBPC was obtained as a pinkish purple solid in a yield of about 419 grams (about 71% of theoretical yield). The purity as measured by HPLC was 98.2%.

EXAMPLE 2 AND COMPARATIVE EXAMPLES 3 TO 8.

In these examples, crude DMBPC of Example 1 was crystallized, or was attempted to be crystallized, using one of the various solvent systems as shown in Table 1.

Crude DMBPC was first dissolved in a first solvent and heated to about a reflux temperature of the solvent to obtain a first solution. The first solution was hot-filtered through a sintered glass funnel, and then mixed with a second solvent at about a reflux temperature of the first solvent. In those comparative examples where a single crystallization is employed, the first solution was cooled and the crystals were collected, if any. Those examples employing the second solvent included a cooling process to permit the DMBPC product to crystallize. In those examples employing a third solvent, the crystalline DMBPC obtained from the previous cooling process was dissolved in the third solvent at about a reflux temperature, which was then allowed to cool and form crystalline DMBPC product.

The crystalline DMBPC obtained was then melt polymerized to form a polycarbonatei A glass polymerization reactor was passivated by soaking it in a bath containing 1 molar aqueous hydrochloric acid solution. After 24 hours, the thoroughly dried and charged with the appropriate amounts of one or more bisphenol monomers and diphenyl carbonate. The reactor was then mounted in a polymerization assembly and checked to ensure that no leaks were present. The required amount of the catalyst solution, as prepared above, was then introduced into the reactor using a syringe. The atmosphere inside the reactor was then evacuated using a vacuum source and then purged with nitrogen. This cycle was repeated 3 times after which the contents of the reactor were heated to melt the monomer mixture.

The general polymerization procedure included melt reacting a 50:50 relative weight ratio/of bisphenol A (hereinafter sometimes referred to as "BPA") and the appropriate type of DMBPC. All reactions were carried out using a mole ratio of, diphenyl carbonate to the total moles of second crystalline DMBPC and BPA of 1.08. The catalyst used was mixture of sodium hydroxide and tetramethylammonium hydroxide taken in a mole ratio of 1:100, respectively. In each case, there was employed $2.5 \times 10^{-4}$ moles of tetramethylammonium hydroxide per mole of the combination of second crystalline DMBPC and BPA.

When the temperature of the mixture reached about 180° C., the stirrer in the reactor was turned on and adjusted to about 40 to about 80 rpm to ensure that the entire solid mass fully melted, a process that usually took about 15 to about 20 minutes. Next, the reaction mixture was heated to about 230° C. while the pressure inside the/reactor was adjusted to about 170 millibar using a vacuum source. This temperature-pressure-time regime was designated as P1. After stirring the reaction mass at this condition for about 1 hour, the reaction temperature was raised to about 270° C. while readjusting the pressure to about 20 millibar. After being maintained at this condition, designated as P2, for about 30 minutes, the temperature of the reaction mixture was raised to about 300° C. while bringing the pressure down to about 1.5 millibar. After allowing the reaction to proceed under these conditions, designated as P3, for about 30 to about 60 minutes, the pressure inside the reactor was brought to atmospheric pressure and the reactor was vented to relieve any excess pressure.

Product is lation was accomplished by breaking the glass nipple at the bottom of the reactor and collecting the material. In the cases where the product was of a very high molecular weight, the hot molten polymer was dropped down by pressurizing the reactor with nitrogen gas.

The resuls of the polymerization process with the crystallized DMBPC are shown in Table 1. The molar ratios of the reactants as well as the reaction conditions were identical for each example and comparative example.

The solvent systems employed and the results obtained are shown in Table 1. The terms "IPA", "$M_w$", "$M_n$" and "PDI" represent isopropanol, weight average molecular weight, number average molecular weight, and polydispersity, respectively. The units. reported for the values shown for $M_w$ and $M_n$ are Daltons.

TABLE 1

| | Solvent System | | | Ratio of first solvent | DMBPC Purity | Polycarbonate | | |
| | | | | | | $M_w$ | $M_n$ | |
| Ex. No. | First solvent | Second solvent | Third solvent | to second solvent (v/v) | (%) | ($\times 10^3$) | ($\times 10^3$) | PDI |
|---|---|---|---|---|---|---|---|---|
| 2 | $CH_3OH$ | Water | Toluene | 80/20 | 99.9 | 41.6 | 20.2 | 2.1 |
| 3* | $CH_3OH$ | — | — | — | — | — | — | — |
| 4* | $C_2H_5OH$ | — | — | — | — | — | — | — |
| 5* | $CH_3OH$ | Toluene | — | 67/33 | — | — | — | — |
| 6* | IPA | Toluene | — | 67/33 | — | — | — | — |
| 7* | Toluene | — | — | — | — | 29.64 | 14.31 | 2.1 |
| 8* | Toluene | Toluene | — | — | 99.3 | 30.45 | 15.4 | 2.1 |

*comparative examples

The results clearly show that high molecular weight polycarbonates can be made using a Process in accordance with the present disclosure. An average molecular weight greater than 30,000 Daltons can be obtained. Employing an alcohol by itself failed to produce any crystallization of DMBPC. These Examples illustrate the effect of the purity of the various types of crystallized DMBPC on the molecular weight and color ofthepolycarbonate obtained by melt polymerization.

EXAMPLE 9.

In this example, the crystallized DMBPC of Example 2 was employed as a monomer for n interfacial polymerization reaction to produce a polycarbonate.

Into a 500 ml Morton flask was placed the second crystalline DMBPC (14.8 g, 50 mmol), BPA (11.4 g, 50 mmol), p-cumylphenol (1.18 g, 5.5 mol %), 200 microliters (ul) of triethylamine, dichloromethane (90 ml) and 90 ml of water. The pH was adjusted to 10.5 with 25-weight percent aqueous sodium hydroxide solution. Phosgene was added at a rate of 0.6 grams/minute until 13.3 g (30 mol % excess) had been added. The polymer solution was then diluted with 30 ml of dichloromethane, and the dichloromethane layer was separated from the aqueous layer, washed with aqueous hydrochloric acid, and then washed with water. The polymer was isolated by hot water precipitation and dried at 110° C. The average weight molecular weight was determined to be Mw=44,400.

A sample of the polycarbonate (0.2 g) was then dissolved in dichloromethane and treated with a 0.1 Normal dichloromethane solution of 4-nitrobenzylpyridine (4-NBP) (1.0 ml), and stirred for about 2 hours. The ultraviolet (UV) absorbance was measured at 440 nanometers with an ultraviolet spectrophotometer, and the residual level of chloroformate was determined to be 0.8 ppm.

Advantageously, when the DMBPC purified from a methanol-water solvent system, and then from toluene is polymerized by the melt process, the polycarbonate produced has a higher molecular weight compared to the DMBPC purified using other solvent systems (Comparative Examples 3–8). Furthermore, when the DMBPC purified from a methanol-water solvent system, and then from toluene was polymerized by the interfacia lmethod, the polycarbonate produced has a molecular weight that is within 10% of the molecular weight of the polycarbonate resulting from the melt polymerization process. Furthermore, the 0.8 ppm of residual chloroformate in the polycarbonate, produced by the interfacial method, is indicative of a relatively low amount of TMBPC impurity. The polycarbonates made by the melt and interfacial methods, as described above, are expected to have enhanced physical properties, and therefore find wider application.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims. All Patents cited herein are incorporated herein by reference.

What is claimed is:

1. A method for purifying 1,1-bis(4'-hydroxy-3'-methylphenyl)cyclohexane comprising:
   dissolving said 1,1-bis(4'-hydroxy-3'-methylphenyl) cyclohexane in a first solvent consisting essentially of an alcohol to form a first solution; filtering said first solution;
   adding a Slecond solvent consisting essentially of water to the filtered first solution to form a second solution, wherein said second solution comprises about 40 parts to about 95 parts of the first solvent per 100 parts of the combined weight of the first and second solvents;
   crystallizing said 1,1-bis(4'-hydroxy-3'-methylphenyl) cyclohexane from said second solution to form a first crystalline product;
   dissolving said first crystalline product in a third solvent to form a third solution, wherein the third solvent comprises an aromatic compound; and
   crystallizing said 1,1-bis(4'-hydroxy-3'-methylphenyl) cyclohexane from said third solution to produce a second crystalline product.

2. The method of claim 1, wherein the aromatic compound comprises a formula $R^1R^2(C_6H_3)R^3$, wherein each $R^1$ group, $R^2$ group, and $R^3$ group is indepen dently selected from the group consisting of chlorine, hydrogen, methyl, ethyl, n-propyl, isopropyl, n-butyl, iso-butyl, and tert-butyl radicals.

3. The method of claim 1, wherein the aromatic compound comprises toluene.

4. The method of claim 1, wherein the alcohol has a formula of $R^4OH$, wherein $R^4$ comprises a $C_1$–$C_4$ alkyl radical.

5. The method of claim 1, wherein the alcohol is methanol.

6. The method of claim 1, wherein dissolving said 1,1-bis(4'-hydroxy-3'-methylphenyl)cyclohexane comprises heating to a temperature of about an ambient temperature to about a reflux temperature of said first solvent.

7. The method of claim 1, wherein said crystallizing to produce a first crystalline product comprises cooling said second solution to a temperature of about ambient to about 5° C.

8. The method of claim 1, wherein dissolving said first crystalline product in the third solvent is performed at a temperature of about ambient to about a reflux temperature of said second solvent.

9. The method of claim 1, wherein crystallizing to produce a second crystalline product comprises cooling said third solution to a temperature of about ambient temperature to about 5° C.

10. The method of claim 1, wherein the second crystalline product comprises less than about 250 parts of any combination of 1-(4'-hydroxy-3'-methylphenyl)-1-(4'-hydroxy-3', 5'-dimethylphenyl)cyclohexane compound and 1,1-bis(4'-hydroxy-3',5'-dimethylphenyl)cyclohexane compound, per million parts of the second-crystalline product.

11. A 1,1-bis(4'-hydroxy-3'-methylphenyl)cyclohexane compound purified in accordance with claim 1.

12. A method of producing a polycarbonate comprising:
melt reacting a reaction mixture at a temperature from about a melting temperature of the reaction mixture to about 350° C. to produce a polycarbonate product, the reaction mixture comprising:
a catalyst composition selected from the group consisting of alkali metal compounds, alkaline earth metal compounds, tetraorganoammonium compounds, tetraorganophosphonium compounds, and mixtures comprising one or more of the foregoing catalysts;
a carbonic acid diester of the formula $(ZO)_2 C=O$, wherein each Z is selected from the group consisting of phenyl, 2,4-dichlorophenyl, 2,4,5-trichlorophenyl, 2-cyantophenyl, o-nitrophenyl, (2-methoxycarbonyl) phenyl; (2-ethoxycarbonyl) phenyl); tolyl, m-cresyl, naphthyl, ethyl, methyl, butyl, cyclohexyl, and combinations comprising one or more of the foregoing groups;
a second crystalline product of 1,1-bis(4'-hydroxy-3'-methylphenyl) cyclohexane formed by dissolving said 1,1-bis(4'-hydroxy-3'-methylphenyl) cyclohexane in a first solvent consisting essentially of water and an alcohol to form a first solution; crystallizing said 1,1-bis(4'-hydroxy-3'-methylphenyl) cyclohlexane from said first solution to produce a first crystalline product; dissolving said first crystalline product in a second solvent comprising a compound having a formula $R^1R^2(C_6H_3)R^3$ to form a second solution;
and crystallizing said 1,1-bis(4'-hydroxy-3'-methylphenyl)cyclohexane from said second solution to produce the second crystalline product; and
at least one aromatic dihydroxy compound comonomer having the formula

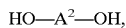
HO—A²—OH, wherein $A^2$ is selected from the group consisting of divalent substituted and unsubstituted aromatic radicals; and
wherein the amount of the catalyst composition comprises about $1 \times 10^{-7}$ to about $2 \times 10^{-3}$ moles for each mole of the second crystalline product and the at least one aromatic dihydroxy compound comonomer; and the carbonic acid diester comprises a mole ratio of about 0.95 to about 1.30 relative to the total moles of the second crystalline product and the at least one aromatic dihydroxy compound comonomer.

13. The method of claim 12, wherein the aromatic dihydroxy comonomer compound is selected from the group consisting of 1,1-bis(4-hydroxyphenyl) methane; 1,1-bis(4-hydroxyphenyl) ethane; bisphenol A; 2,2-bis(4-hydroxyphenyl) butane; 2,2-bis(4-hydroxyphenyl) octane; 1,1-bis(4-hydroxyphenyl) propane; 1,1-bis(4-hydroxyphenyl) n-butane; bis(4-hydroxyphenyl) phenylmethane; 2,2-bis(4-hydroxy-3-methylphenyl) propane; 1,1-bis(4-hydroxy-t-butylphenyl) propane; 2,2-bis(4-hydroxy-3-bromophenyl) propane; 1,1-bis(4-hydroxyphenyl) cyclopentane; 9,9'-bis(4-hydroxyphenyl) fluorene; 9,9'-bis(4-hydroxy-3-methylphenyl) fluorene; 4,4'-biphenol; 1,1-bis(4-hydroxyphenyl) cyclohexane; resorcinol, 4,4'-(1-decylidene)-bisphenol, 2,2-bis(3-sec-butyl-4-hydroxyphenyl)propane, and combinations comprising one or more of the foregoing compounds.

14. A polycarbonate produced in accordance with the method of claim 12, wherein said polycarbonate has a weight average molecular weight of at least about 30,000.

15. An article comprising the polycarbonate of claim 14.

16. A method of producing a polycarbonate comprising:
interfacially reacting a reaction mixture at a temperature from about 5° C. to about 50° C., and an initial pH from about 9.5 to about 11.0 to produce a polycarbonate product, the reaction mixture comprising:
phosgene,
a substituted or an unsubstituted monohydric phenol having the formula $R^5(C_6H_4)OH$, wherein $R^5$ comprises hydrogen and $C_1$–$C_{12}$ linear and branched alkyl and cycloalkyl groups;
a tertiary amine having the formula $R^6R^7R^8N$, wherein $R^6$, $R^7$, and $R^8$ selected from $C_1$–$C_{12}$ linear and branched alkyl radicals;
at least one halogen-containing hydrocarbon solvent;
water,
an alkali metal hydroxide selected from the group consisting of lithium hydroxide, sodium hydroxide, potassium hydroxide, rubidium hydroxide, and cesium hydroxide;
a second crystalline product of 1,1-bis(4'-hydroxy-3'-methylphenyl) cyclohexane formed by dissolving said 1,1-bis(4'-hydroxy-3'-methylphenyl) cyclohexane in a first solvent consisting essentially of water and an alcohol to form a first solution; crystallizing said 1,1-bis(4'-hydroxy-3'-methylphenyl) cyclohexane from said first solution to produce a first crystalline product;
dissolving said first crystalline product in a second solvent comprising a compound having theformula $R^1R^2(C_6H_3)R^3$ to form a second solution;
and crystallizing said 1,1-bis(4'-hydroxy-3'-methylphenyl)cyclohexane from said second solution to produce the second crystalline product;
at least one aromatic dihydroxy compound comonomer having the formula:

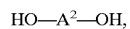
HO—A²—OH, wherein $A^2$ is selected from the group consisting of divalent substituted and unsubstituted aromatic radicals; and
wherein the phosgene is used in an amount from about stoichiometric to about 50 mole percent excess relative to the total moles of second crystalline product and the at least one aromatic dihydroxy compound comonomer.

17. The method of claim 16, wherein the monohydric phenol is 4-cumylphenol.

18. The method of claim 16, wherein the halogen-containing organic solvent contains at least one chlorine atom, and comprises chlorinated $C_1$–$C_{12}$ linear and branched aliphatic hydrocarbons, and chlorinated $C_6$–$C_9$ aromatic hydrocarbons.

19. The method of claim 16, wherein the tertiary amine is selected from the group coisisting of trimethylamine, triethylamine, tri-n-propylamine, tri-n-butylamine, methyldiisopropylamine, N-methylpiperidine, and dimethylbutylamine.

20. The method of claim 16, wherein the aromatic dihydroxy comonorner compound is selected from the group consisting of 1,1-bis(4-hydroxyphenyl) methane; 1,1-bis(4-hydroxyphenyl) ethane; bisphenol A; 2,2-bis(4-hydroxyphenyl) butane; 2,2-bis(4-hydroxyphenyl) octane; 1,1-bis(4-hydroxyphenyl) propane; 1,1-bis(4-hydroxyphenyl) n-butane; bis(4-hydroxyphenyl) phenylmethane; 2,2-bis(4-hydroxy-3-methylphenyl) propane; 1,1-bis(4-hydroxy-t-butylphenyl) propane; 2,2-bis(4-hydroxy-3-bromophenyl) propane; 1,1-bis(4-hydroxyphenyl) cyclopentane; 9,9'-bis(4-hydroxyphenyl) fluorene; 9,9'-bis(4-hydroxy-3-methylphenyl) fluorene; 4,4'-biphenol; 1,1-bis(4-hydroxyphenyl) cyclohexane; resorcinol, 4,4'-(1-decylidene)-bisphenol, 2,2-bis(3-sec-butyl-4-hydroxyphenyl)propane, and combinations comprising one or more of the foregoing compounds.

21. A polycarbonate produced in accordance with the method of claim 16, wherein the polycarbonate has a weight average molecular weight of at least about 30,000 and a chloroformate content from about 0.5 parts to about 1.5 part per million parts of said polycarbonate.

22. An article comprising the polycarbonate of claim 21.

* * * * *